US010400207B2

(12) United States Patent
Segard

(10) Patent No.: US 10,400,207 B2
(45) Date of Patent: Sep. 3, 2019

(54) BIOREACTOR

(71) Applicant: ROQUETTE FRERES, Lestrem (FR)

(72) Inventor: David Segard, Lestrem (FR)

(73) Assignee: Roquette Freres, Lestrem (FR)

( * ) Notice: Subject to any disclaimer, the term of this patent is extended or adjusted under 35 U.S.C. 154(b) by 630 days.

(21) Appl. No.: 14/776,225

(22) PCT Filed: Mar. 12, 2014

(86) PCT No.: PCT/FR2014/050555
§ 371 (c)(1),
(2) Date: Sep. 14, 2015

(87) PCT Pub. No.: WO2014/140476
PCT Pub. Date: Sep. 18, 2014

(65) Prior Publication Data
US 2016/0032235 A1 Feb. 4, 2016

(30) Foreign Application Priority Data

Mar. 13, 2013 (FR) ...................................... 13 52236

(51) Int. Cl.
*C12M 1/00* (2006.01)
*C12M 1/06* (2006.01)
(Continued)

(52) U.S. Cl.
CPC ............ *C12M 41/14* (2013.01); *C12M 21/02* (2013.01); *C12M 23/46* (2013.01); *C12M 27/02* (2013.01); *C12M 41/24* (2013.01); *C12N 1/12* (2013.01)

(58) Field of Classification Search
CPC ...... C12M 41/14; C12M 23/46; C12M 27/02; C12M 41/24; C12M 1/12
See application file for complete search history.

(56) References Cited

U.S. PATENT DOCUMENTS 2,973,944 A * 3/1961 Etter ..................... F28D 1/0213
165/109.1
3,978,918 A * 9/1976 Nagatomo ............ B01F 15/066
165/109.1
(Continued)

FOREIGN PATENT DOCUMENTS

CN 1475562 A 2/2004
CN 201 476 623 U 5/2010
(Continued)

OTHER PUBLICATIONS

Chen; CN201476623 English Translation from Google Patents Jan. 2018 (Year: 2018).*
(Continued)

*Primary Examiner* — William H. Beisner
*Assistant Examiner* — Danielle B Henkel

(57) ABSTRACT

A bioreactor (1) includes a container body (2), whose inner walls together define an internal volume for receiving biomass, a cooling and/or heating duct (3, 3', 3") whose outer wall is intended to be in direct contact with the biomass, disposed in the internal volume, and extending at least over a portion of the length in the form of a helicoid, fastening elements (4) for supporting the cooling and/or heating duct (3, 3', 3") and fastening same to the container body (2), in several receiving positions along the helicoid. The duct is fastened, at the receiving positions, by connectors and one or a plurality of supports, and for each receiving position by a first weld between the connector and the support and a second weld between the connector and the duct.

17 Claims, 5 Drawing Sheets

(51) Int. Cl.
　　　*C12M 3/00*　　　(2006.01)
　　　*C12N 1/12*　　　(2006.01)
　　　*C12M 1/02*　　　(2006.01)

(56) References Cited

U.S. PATENT DOCUMENTS

| | | | | |
|---|---|---|---|---|
| 5,780,804 | A | * | 7/1998 | White .................. B23K 9/0061 219/121.43 |
| 2010/0190227 | A1 | * | 7/2010 | Dauth .................... C12M 21/02 435/168 |

FOREIGN PATENT DOCUMENTS

| | | |
|---|---|---|
| CN | 201637304 U | 11/2010 |
| DE | 27 53 388 A1 | 7/1978 |
| JP | 2006014627 A | 1/2006 |

OTHER PUBLICATIONS

International Search Report, dated Oct. 23, 2014, from corresponding PCT application.
The Chinese Office Action, dated Oct. 25, 2016, in the related Chinese Patent Appl. No. 201480014163.3.

* cited by examiner

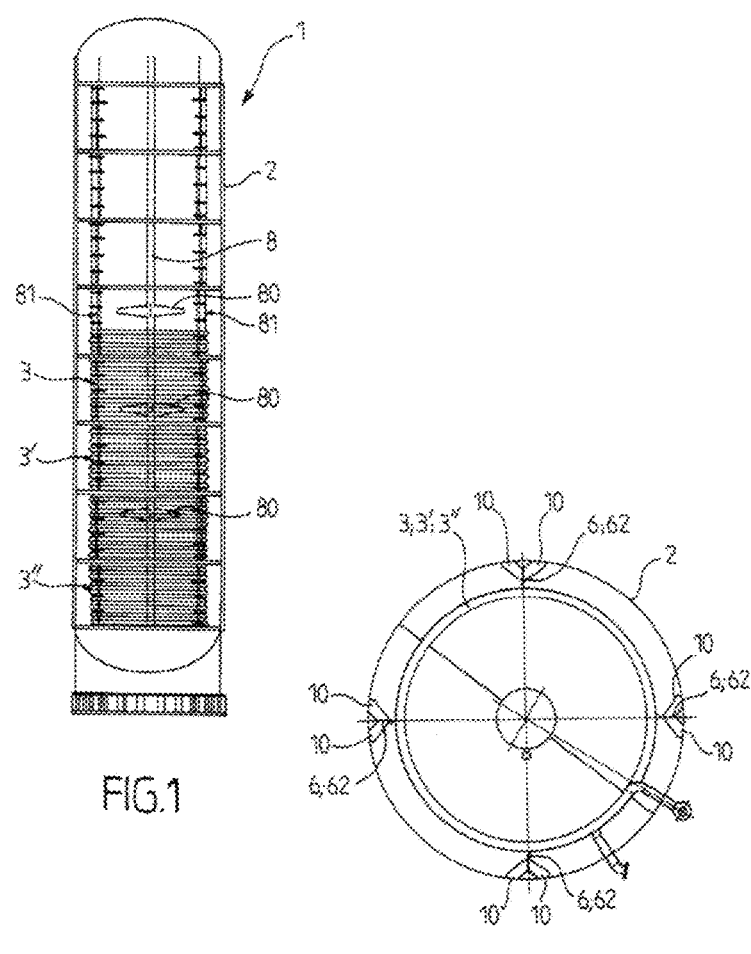

BIOREACTOR

The invention relates to any type of bioreactor and will have a particular application for implementation of complex fermentations which are sensitive to contamination, or also for implementation of biochemical or biological reactions.

The field of the invention is that of bioreactors, and more particularly that of fermenters which permit implementation of discontinuous fermentations which are known as the batch type, semi-continuous fermentations which are known as the fed-batch type, or continuous fermentations.

The invention concerns more particularly reactors on a pilot or industrial scale which permit large volumes of production, and the containers of which can reach capacities of between 20 m$^3$ and several hundred m$^3$.

Bioreactors are used to produce cellular biomass (yeasts, bacteria, microscopic fungi, microalgae, and animal and vegetable cells), and/or to ensure the production of useful metabolites (proteins, vitamins, antibiotics, polyols, etc.).

In the prior art, reactors are thus known on a pilot or industrial scale, with a particular application for this use.

Reactors of this type conventionally comprise a container body with a large volume, which is very often cylindrical with a vertical axis, inside which there takes place the biological reaction (fermentation) or biochemical reaction (enzymatic), often under strong agitation.

Agitation means are provided inside the container body, and conventionally comprise a rotor, generally with an axis which is coaxial with that of the container body, supporting blades which are designed to agitate the biomass strongly. This rotor is rotated relative to the container body by a gear motor. The agitation means also comprise counter-blades which project towards the center of the container, and are rendered integral around the rotor in positions which are fixed relative to the container body.

In order to be able to control the temperature of the reaction, it is also known to cool or heat the reactor from the exterior and/or from the interior by means of one or a plurality of exchangers outside or inside the container body. In each exchanger there circulates a fluid, which conveys heat and/or cold, as required.

Very often during the exothermal fermentation reaction one or a plurality of cold units permit the circulation of a fluid which conveys cold in the exchangers, and thus prevents the reaction temperature from being too high.

The exchanger outside the container can be constituted by a double envelope of the container body, inside which the fluid which conveys heat/cold circulates. An external exchanger has the advantage of leaving the volume inside the container body free. On the other hand, the performance of the heat exchange is lower than that of an internal exchanger.

This is why an exchanger inside the container is often necessary when the temperature control of the reaction requires a strong heat exchange. The internal exchangers comprise one or a plurality of ducts which extend in the inner volume of the container body. The outer wall of the ducts of the internal exchanger is in direct contact with the biomass.

An internal exchanger is thus known in the prior art, in the form of a duct which extends in the form of a helicoid, also known as a pipe coil, the axis of the helicoid generally being coaxial with the axis of the container body.

During the reaction inside the container, this duct can be deformed strongly under the action of the pressure stresses caused by the strong internal agitation, as well as by the stresses caused by the retraction and/or expansion of the duct generated by the temperature variations.

In order to limit this deformation, it is known to support this duct not only at the input connection piece and the output connection piece, but also at various receipt points along the helicoid.

According to the known prior art, the pipe coil is conventionally supported by means of U-bolts which straddle the duct at the various receipt points along the helicoid, and are secured on the inner wall directly, or indirectly by means of supports.

Document CN201476623U discloses and illustrates a variant of this method for securing the helicoid duct by means of U-bolts.

A reactor of this type comprising an inner pipe coil which is supported by U-bolts is commonly used for batch-type fermentations. The applicant thus uses reactors of this type for the production of useful metabolites.

The applicant has recently used bioreactors of this type for a new application, i.e. the production of cell biomasses, and more particularly the culture of microalgae of the *Chlorella* type.

More particularly, the objective was to produce the biomass of microalgae in heterotrophic conditions, i.e. in the dark, in the presence of a carbonated source assimilable by said microalga.

During this test, these single-cell organisms were found to be very sensitive to contamination which, when it occurred, rapidly got the upper hand over the cultivated organisms. In fact, the speed of growth of the contaminants, and in particular bacterial contaminants, is far greater than that of the microalgae.

At present there are no economically viable solutions for separating the biomass of microalgae from its contaminants. Thus, in practice, when contamination occurs, the content of the bioreactor is entirely emptied and discarded, the reactor then needing to be cleaned and sterilized before the implementation of a new fermentation reaction.

After various tests, and according to the findings of the inventor, the applicant ascertained that the configuration of the bioreactors with an internal exchanger according to the prior art is too favorable to the occurrence and development of contamination, and is therefore unsuitable for the long-lasting culture of single-cell organisms, in particular of the microalgae type.

The objective of the present invention is to eliminate the aforementioned disadvantages by proposing a bioreactor which can permit control of the temperature of the reaction inside the container, which has a satisfactory thermal performance, and permits implementation of complex fermentations which are sensitive to contamination.

More particularly, the objective of the present invention is to propose a reactor of this type which prevents, or at the very least limits, the interruptions of production.

Other objectives and advantages of the invention will become more clearly apparent from the following description which is provided purely by way of indication, and is not intended to limit the invention.

Thus, the invention relates to a bioreactor comprising:
- a container body, the inner walls of which define between one another an inner volume for receipt of the biomass;
- a cooling and/or heating duct, the outer wall of which is designed to be in direct contact with the biomass disposed in said inner volume, and extending along at least part of the length in the form of a helicoid;

securing means which ensure the support of said cooling and/or heating duct, and securing of the duct on the container body in a plurality of receipt positions along the helicoid.

According to the invention, said securing means comprise:

connectors, which are preferably tubular or semi-tubular, and envelope said duct from the exterior, locally, at said various receipt positions along the helicoid;

one or a plurality of supports (plates, profiles, etc.) rendered integral with the inner wall of the container body, and projecting towards the center of the container body, said support(s) having a plurality of bores with a form complementary to the outer dimensions of the connectors, provided at said various receipt positions along the helicoid, said bores receiving said connectors, and wherein said cooling and/or heating duct is rendered integral at each of said receipt positions by means of:

a first weld which connects the corresponding connector and the corresponding support (plate, profile, etc.), said first weld extending along the edges of the corresponding bore, on the two sides of said corresponding support (plate, profile, etc.), and a second weld which connects the corresponding connector and the cooling and/or heating duct, said second weld extending along the edges of said connector.

Preferably, said first weld and said second weld are welds produced by addition of metal.

It will be appreciated that the term "weld" used can comprise one welding bead or a plurality of welding beads, as is known to persons skilled in the art in general.

According to optional characteristics, taken alone or in combination:

the or each metal welding bead of said first weld and/or of said second weld forms a hollow fillet, said welds preferably being polished;

each of the bores opens at an edge of said support (plate, profile, etc.) or of one of said supports (plates, profiles, etc.);

the bores open towards the center of the container body;

said first weld is constituted by a continuous welding line with a closed trajectory which runs at the edges of the bore of the two sides of said corresponding support (plate, profile, etc.), as well as on the cant of said corresponding support (plate, profile, etc.), at the upper part and at the lower part of said cooling and/or heating duct;

the connectors have a semi-tubular form, and said second weld is constituted by a continuous welding line with a closed trajectory which runs at the edges of the connector, along the longitudinal edges of the connector, as well as along the arched edges of said connector;

when the bioreactor has agitation means, they comprise firstly a rotor inside the container body, which rotor is mobile in rotation relative to the container body, the rotor having blades, and secondly counter-blades which project towards the center of the container, and are rendered integral in fixed positions relative to the container body;

the counter-blades of said agitation means can comprise said supports (plates, profiles, etc.) or said support (plate, profile, etc.) of said securing means (as will be described in an example hereinafter);

the bores are so-called first bores, said support(s) having, in addition to said first bores at said various positions for receipt of the helicoid, second bores with dimensions which are superabundant relative to the diameter of said duct, said duct passing through said second bores such as to leave play which permits free deformation of said duct;

the reactor has a plurality of said supports (plates, profiles, etc.) distributed angularly on the inner circumference of the container body, and each oriented along their longitudinal axis according to the height of the container body, and each extending corresponding to the height of the helicoid;

said support (plate, profile, etc.) or each of the supports (plates, profiles, etc.) has an outer edge facing the lateral inner wall of the container, and said securing means comprise counter-braces which ensure that said support (plate, profile, etc.) or each of said supports (plates, profiles, etc.) is rendered integral with the lateral inner wall of the container body, creating an inter-space between the outer edge of said corresponding support (plate, profile, etc.) and the inner wall of the container body;

each counter-brace is welded respectively on said corresponding support (plate, profile, etc.) and on the inner wall of the container body, and, by means of addition of metal, said welds have a metal welding bead forming a hollow fillet, said welds being polished;

the bioreactor can be provided with a device for cooling/heating the container body from the exterior, by means of circulation of a fluid which conveys heat/cold.

The invention will be better understood by reading the following description accompanied by the drawings, in which:

FIG. 1 is a transparent view of a bioreactor in accordance with the invention according to an embodiment for which the supports are in the form of plates;

FIG. 1a is a view from below of the bioreactor according to FIG. 1;

Figure 4:
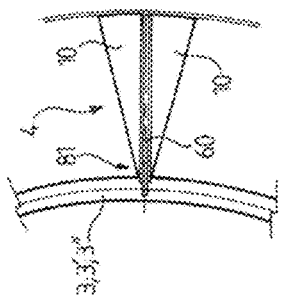
FIG. 4 is a view from above of said securing means as illustrated in FIG. 2.
Figure 3:
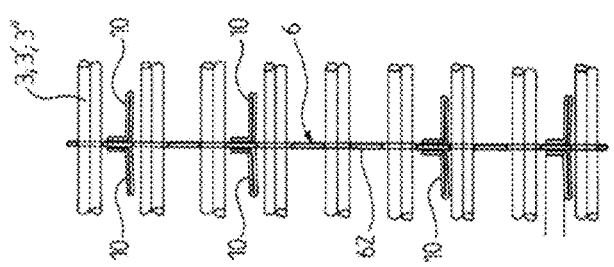
FIG. 3 is a front view of said securing means as illustrated in FIG. 2.

The invention is derived from the finding by the inventor that the bioreactors with an internal exchanger / internal exchangers according to the prior art create within the body of the container of the reactor numerous interstitial areas and/or areas which cannot be emptied which are favorable to depositing of material, in particular organic material, and on which contamination occurs and develops.

According to the findings of the inventor, these interstitial areas are located to a large extent at the exchanger and/or its receipt areas.

In the case of a pipe coil internal exchanger in particular, these interstitial areas and/or areas which cannot be cleaned are situated on the structure with U-bolts which supports the helical duct, in particular at each gap formed between one of the U-bolts and the duct, and also at the supports.

In order to remedy this problem, the present applicant could have chosen simply to eliminate this internal exchanger and replace it by an external exchanger, but this solution was not selected because of the poorer coefficient of transfer of an external exchanger, and also because of the complexity of keeping this type of installation in hygienic conditions, and above all satisfactory aseptic conditions.

On the contrary, the present applicant decided to design a bioreactor, the internal exchanger of which and its support prevent, or at the very least limit considerably or impede, the risks of development of contaminants within the reactor, whilst facilitating its cleanability.

Thus, the invention relates to a bioreactor 1 comprising:
- a container body 2, the inner walls of which define between one another an inner volume for receipt of the biomass;
- a cooling and/or heating duct 3,3',3", the outer wall of which is designed to be in direct contact with the biomass disposed in said inner volume, and extending along at least part of the length in the form of a helicoid;
- securing means 4 which ensure the support of said cooling and/or heating duct 3,3',3", and securing of the duct on the container body 2 in a plurality of receipt positions along the helicoid.

The cooling and/or heating duct 3,3',3" is thus supported not only at the input connection piece and the output connection piece, but also in said plurality of receipt positions.

A fluid which conveys heat or cold, in particular water, is invented to circulate in said duct, the fluid which conveys cold being able to be obtained by means of a cold unit or by means of a boiler or by any other means which permits the removal or addition of calories.

The container body preferably has a cylindrical lateral wall. The bioreactor can comprise a cooling and/or heating duct, or a plurality of ducts 3,3',3" according to the non-limiting embodiment illustrated. The helicoid(s) preferably has/have an axis which is coaxial with the axis of the cylindrical container body.

These ducts 3,3',3" can extend respectively on three levels with different heights, preferably without covering, the helical ducts preferably having the same diameters. Optionally, according to another embodiment not illustrated, the helical ducts with the same diameter can be imbricated.

Said ducts 3,3',3" of the internal exchangers can be situated on the lower part of the container body only, for example on the lower half according to the embodiment illustrated in FIG. 1, the bioreactor being without an internal exchanger in the upper part of the container.

According to the invention, said securing means comprise:
- connectors 5, which are preferably tubular or semi-tubular, and envelope said duct 3,3',3" from the exterior, locally, at said various receipt positions along the helicoid;
- one or a plurality of supports 6 rendered integral with the inner wall of the container body 2, and projecting towards the center of the container body, said support(s) having a plurality of bores 7 with a form complementary to the outer dimensions of the connectors 5, provided at said various receipt positions along the helicoid, said bores 7 receiving said connectors 5.

Said cooling and/or heating duct 3,3',3" is rendered integral at each of said receipt positions by means of:
- a first weld S1 which connects the corresponding connector 5 and said corresponding support 6, said first weld S1 extending along the edges of the corresponding bore 7, on the two sides of said corresponding support 6, and
- a second weld S2 which connects the corresponding connector 5 and the cooling and/or heating duct 3, 3', 3", said second weld S2 extending along the edges of said connector 5.

Said first weld S1 and said second weld S2 are welds produced by addition of metal. The metal welding beads of the first and second welds S1, S2 advantageously make it possible to eliminate any interstitial area between firstly the duct 3, 3', 3" and the connector 5, and secondly the connector 5 and the support 6.

According to the invention, the duct is thus welded on said support or on each of the supports 6 indirectly by means of the connectors 5, the length of each of which extends locally along the duct 3, 3',3", preferably on both sides of the corresponding support 6. This arrangement makes it possible to select a duct thickness which is smaller than that which would be necessary if the duct were welded directly on said support, without a connector.

Preferably, the or each metal welding bead of said first weld S1 and/or of said second weld S2 forms a hollow fillet 11, said welds S1, S2 preferably being polished.

During the operations of securing of the duct, the welder produces firstly at least one welding bead for the first weld S1, and at least one second welding bead for the second weld S2. These beads are then ground in order to form the hollow fillets 11. Fillets of this type make it possible to eliminate the sharp angles which constitute an equivalent number of incipient breaks, and make it possible to ensure better cleanability. For this purpose, the fillets 11 have a radius which is preferably larger than 5 mm. The welds are then polished in order to eliminate the roughness.

The mechanical connection which is thus created between the duct 3, 3', 3" and said support(s) 6 is advantageously without roughness, and without an interstitial area which would assist deposits, in particular organic deposits.

The support(s) 6 can be in the form of plates 62 (see by way of non-limiting example FIGS. 1 to 8), or in the form of tubular or semi-tubular profiles 63.

According to the non-limiting example in FIGS. 11 to 14, the profile 63 can be semi-tubular with a cross section in the form of a "V", the bore(s) 7 opening and being situated at the apex of the "V".

According to one embodiment (not illustrated), each of the bores can have a closed, substantially circular cross section, the connectors then being tubular. In this embodiment, each connector is welded on said support (plate, profile, etc.) by means of two distinct circular welding beads of said first weld S1. These two welding beads are situated on each side C1, C2 of the support (plate, profile, etc.), joining the cylindrical wall of the connector and the support (plate, profile, etc.) along the circular bore. In addition, each connector is welded on the duct by means of two circular welding beads of the second weld, joining the two circular edges of the connector to the cooling and/or heating duct.

According to another embodiment illustrated, which facilitates the assembly of the duct on its support, each of the bores 7 with a semi-circular form opens at an edge of the support 6 or one of the supports 6 (plate 62, profile 63, etc.).

For example, and according to the embodiments illustrated, the bores 7 open towards the center of the container body 2.

Said first weld S1 can then be constituted by a continuous welding line with a closed trajectory which runs (see FIGS. 5 to 8 in the case when the supports are plates 62, and FIGS. 12 to 14 in the case when the supports are profiles 63) at the edges of the semi-circular bore 7, of the two sides C1, C2 of the corresponding support 6, as well as on the cant 60 of the corresponding support, at the upper part and at the lower part of said cooling and/or heating duct 3, 3', 3".

Figures 8, 9:
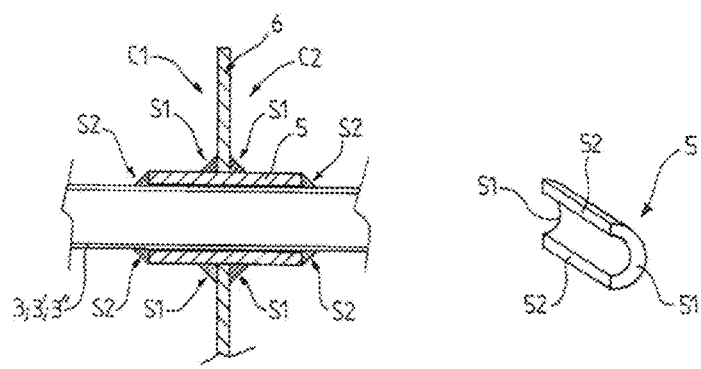
FIG. 8 is a view according to the cross section VII-VII in FIG. 7.
FIG. 9 is a detailed view of a semi-tubular connector.

The connectors 5 can then have a semi-tubular form as illustrated in FIG. 8. In this case, said second weld S2 can be constituted by a continuous welding line with a closed trajectory which runs at the edges of the connector, along the longitudinal edges 52 of the connector 5, as well as along the arched edges 51 of said connector (see FIGS. 5 to 8).

Figure 10:
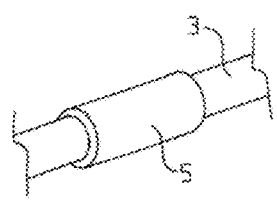
FIG. 10 is a detailed view of a tubular connector enveloping the duct.
Figure 11:
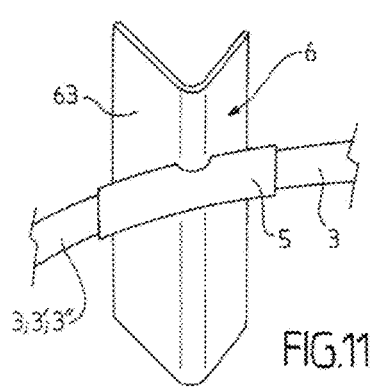
FIG. 11 is a view in perspective of a support taking the form of a semi-tubular profile.
Figure 12:
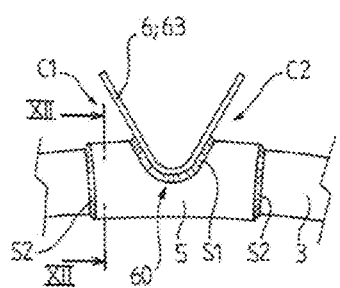
FIG. 12 is a view from above of FIG. 11.
Figure 13:
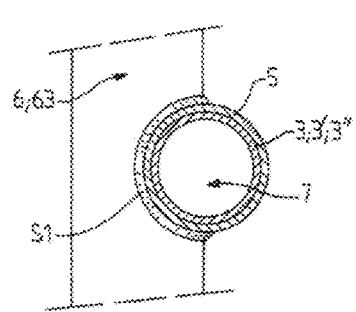
FIG. 13 is a view according to the cross section XII-XII as illustrated in FIG. 12.
Figure 14:
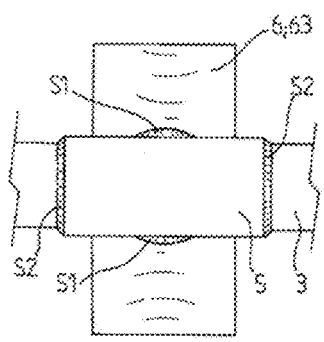
FIG. 14 is a front view of FIG. 11.

Alternatively, the connectors 5 can have a tubular form as illustrated in FIG. 10. Each connector 5 is then welded on the duct by means of two circular welding beads which are distinct from the second weld S2 which joins the two circular edges of the connector to the cooling and/or heating duct (see FIG. 12).

According to one embodiment, the bioreactor can have agitation means, comprising in particular:
 a rotor 8 inside the container body 2, which rotor is mobile in rotation relative to the container body 2, the rotor having blades 80;
 counter-blades 81 which project towards the center of the container, and are rendered integral in fixed positions relative to the container body 2.

According to a particularly advantageous embodiment, the counter-blades 81 of said agitation means comprise said support 6 or said supports 6 (plates 62, profiles 63, etc.) of said securing means. According to this embodiment, said support(s) 6 thus combine a function of support of the cooling and/or heating duct 3,3', 3", and a function of counter-blade for agitation of the biomass.

According to an advantageous embodiment, the counter-blades are constituted entirely by said supports 6 of said securing means, and for example by the plates 6 according to the embodiment in FIGS. 1 to 8.

In the knowledge of the applicant, and in the bioreactors according to the prior art, the support of the helical duct of the internal exchanger on the one hand, and the counter-blades of said agitation means on the other hand, are constituted by distinct elements. In this case, and according to the prior art known by the applicant, the helical duct is offset radially, very often towards the center of the duct, relative to the counter-blades.

According to this advantageous embodiment of the invention, the helical duct and the supports (plates, profiles, etc.) are situated radially at the same level, with said support (plate, profile, etc.) or said supports (plates, profiles, etc.) of the securing means not creating an additional surface in the container which assists deposits.

Preferably, the securing means comprise a plurality of said supports 6 (plates 62, profiles 63, etc.) distributed angularly on the inner circumference of the container body, and each oriented along their longitudinal axis in accordance with the height of the container body, and each extending at least corresponding to the height of the helicoid.

According to a preferred embodiment, the securing means are distributed regularly on the inner circumference of the container body.

The number and distribution of the receipt points of the helicoid are preferably selected as a compromise between stress on the duct / receipt support 6 connection, and deformation of the cooling and/or heating duct 3,3',3". It is desirable to give precedence to the solution with the lowest stress, whilst ensuring that the expansion/retraction of the duct is not impeded during the transitory phases.

The receipt points of the helicoid are preferably regularly distributed along the duct every X turns of the helicoid, X being able to be contained between ¼ and ¾, such as, for example, ⅓ of a turn or ⅔ of a turn. According to this value, in certain cases the duct may not be systematically supported each time it passes in the vicinity of the supports 6 (plates, profiles, etc.).

In this case, said support(s) 6 (plates, profiles, etc.) can have, in addition to the bores 7, known as the first bores 7, at said various positions for receipt of the helicoid, second bores 9 with dimensions which are larger than the diameter of said duct. Said duct passes through the second bores 9, such as to leave play which permits free deformation of said duct, without risk of the duct being damaged in contact with the support 6, and in particular with the cant 60 of the plate 62. Play of this type can be more than 1 cm, such as, for example, 1.5 cm.

Figure 2:
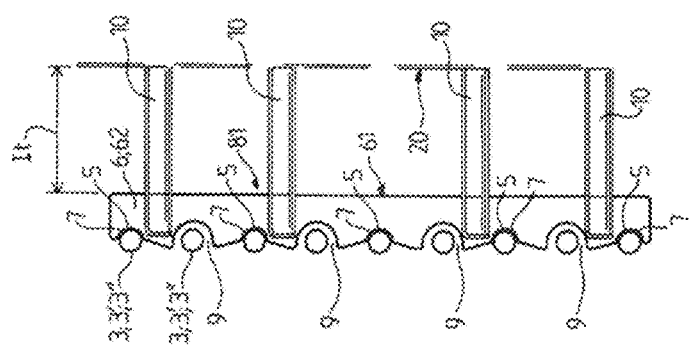
FIG. 2 is a detailed view from the side according to a vertical cross section, illustrating said securing means according to an embodiment of the invention.
Figure 5:
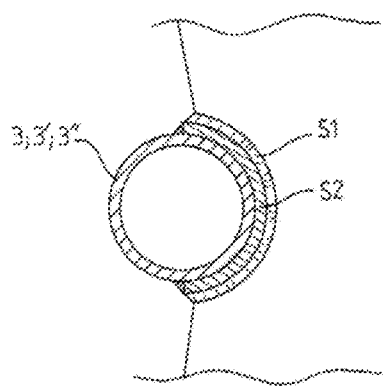
FIG. 5 is a detailed view illustrating said first and second weld at one of the receipt points of the helicoid.
Figure 6:
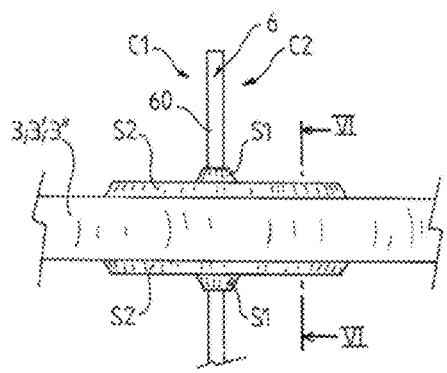
FIG. 6 is a front view of the receipt point of the helicoid in FIG. 5.
Figures 7, 7A:
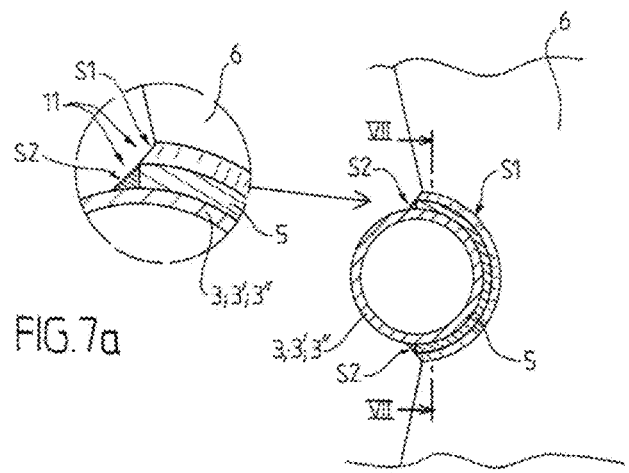
FIG. 7 is a view according to the cross section VI-VI in FIG. 6.
FIG. 7a is a detailed view of FIG. 7.

According to one embodiment, illustrated in a non-limiting example in FIG. 2, each support 6 can have the first bores 7 and the second bores 9 alternately on its height. In the case when one or more of the counter-blades 81 is/are distinct from said supports (plates 62, profile 63, etc.), the or each counter-blade can have such second bores 9 in order to be situated with the same radius as said support(s) in the container body.

Preferably the support(s) 6 (plates 62, profiles 63, etc.) and/or the counter-blades 81 of said agitation means do not extend directly from the lateral wall of the container body, but on the contrary are offset from the latter.

Thus, and according to an embodiment illustrated in FIG. 2, each of the supports 6 (plate 62, profile 63, etc.) thus has an outer edge 61 facing the lateral inner wall 20 of the container body, and said securing means 4 comprise counter-braces 10 which ensure that the support 6 or each of said supports 6 is rendered integral with the inner wall of the container body, creating an inter-space It between the outer edge 61 of the corresponding support 6, and the inner wall 20 of the container body.

Offsetting of this type of the supports 6 and/or of the counter-blades 81 makes it possible to prevent the creation of areas where the biomass is stagnant in the reactor during the agitation, and thus to ensure homogenous agitation of the biomass within the container.

Each counter-brace 10 is preferably welded respectively on the corresponding support 6 and on the inner wall 20 of the body 2. By means of addition of metal, said welds have a metal welding bead forming a hollow fillet with a radius preferably larger than 5 mm, said welds preferably being polished. In addition to said cooling and/or heating duct, the bioreactor can comprise, inside the container body, a device for cooling/heating the container body from the exterior, by means of circulation of a fluid which conveys heat/cold.

This external device can comprise a double envelope on the container body, or any other external exchanger known to persons skilled in the art.

The bioreactor according to the invention has a particular application for implementation of a fermentation method of the batch, fed-batch or continuous type, and more particularly for the implementation of biological or biochemical reactions which are sensitive to contamination.

A reactor of this type is designed in particular for the production of cell biomasses, and more particularly for the culture of microalgae of the *Chlorella* type.

A fermentation cycle can begin with cleaning of the bioreactor chemically and/or physically (sterilization), followed by filling of the container body with nutritive substances which can also be sterilized before or after their introduction, then with the biological catalyst, in particular a cellular biomass, which is then supplied with nutritive, and particularly carbonated, substances during the fermentation, and is agitated, preferably continually.

Biological reactions of this type can last for several days. At the end of the process, the biomass and/or the useful compound is recuperated by emptying the container.

The bioreactor according to the invention is, advantageously, as far as possible without any area, in particular an interstitial area within the container body, which would be favorable to the development of contamination. The reactor is thus designed to prevent the depositing of substances, in particular organic substances, during the fermentation reaction, in particular by means of the action of the internal agitation. It advantageously makes it possible to prevent, or to limit considerably, production interruptions for the maintenance and cleaning of the container.

In a manner known per se, the bioreactor can comprise a supply opening for the products and the auxiliary substances (nutriments, acid/base for regulation of the pH, addition of anti-foaming agent, etc.), an output for discharge of the products, various sensors, such as sensors for pH, temperatures, gas ($O_2$), etc., as well as a control/command system, or an air diffuser (known as a "bubbler system") in the lower part, hatches, and it can be with or without lighting, or any other accessory which is usually encountered in reactors of this type.

The invention has an application for the production of cell biomasses selected from the group constituted by cells of the so-called "wild" type or mutated by techniques of the random mutagenesis type or by genetic engineering.

The invention has an application in the field of the human or animal foodstuffs industries, biotechnology industries, pharmaceutical and cosmetics industries, and in the field of biofuels and chemistry.

It will be appreciated that other embodiments could have been envisaged without departing from the context of the invention as defined by the following claims.

LIST OF PARTS

1. Bioreactor
2. Container body
3, 3', 3" Cooling and/or heating duct
4. Securing means
5. Connectors
6. Support(s)
7. Bores (First bores)
8. Rotor
9. Bores (Second bores)
10. Counter-braces
11. Fillet (Welds)
20. Inner wall
51. Arched edges
52. Longitudinal edges
60. Cant (support 6)
61. Outer edge (support 6)
62. Plates (supports 6)
63. Profile (support 6)
80. Blades (Rotor 8)
81. Counter-blades
C1,C2 Support sides
It. Inter-space
S1. First weld
S2. Second weld

The invention claimed is:

1. A bioreactor (1) comprising:
    a container body (2), the inner walls of which define between one another an inner volume for receipt of the biomass;
    a cooling and/or heating duct (3,3',3"), the outer wall of which is designed to be in direct contact with the biomass disposed in said inner volume, and extending along at least part of the length in the form of a helicoid;
    securing means (4) which ensure the support of said cooling and/or heating duct (3,3',3"), and securing of the duct on the container body (2) in a plurality of receipt positions along the helicoids,
    wherein said securing means comprise:
        connectors (5), which are tubular or semi-tubular comprising each an inner tubular or semi-tubular surface and an outer tubular or semi-tubular surface, and enveloping said duct (3,3',3") from the exterior, locally, at said various receipt positions along the helicoid;
        one or a plurality of supports (6) rendered integral with the inner wall of the container body (2), and projecting towards the center of the container body, said support(s) (6) having a plurality of bores (7) with a form complementary to the outer dimensions of the outer tubular or semi tubular surface of said connectors (5), provided at said various receipt positions along the helicoid, said bores (7) receiving said connectors (5),
    and wherein said cooling and/or heating duct (3,3'3") is rendered integral at each of said receipt positions by:
        a first weld (S1) which connects the corresponding connector (5) and the corresponding support (6), said first weld (S1) extending along the edges of the corresponding bore (7), on the two sides of said corresponding support (6), said first weld (S1) connecting the outer tubular or semi tubular surface of said connectors (5) with the corresponding surface of the corresponding support (6) along the edges of the corresponding bore (7),
        a second weld (S2) which connects the corresponding connector (5) and the cooling and/or heating duct (3,3',3"), said second weld (S2) extending along the edges of said connector (5),
    and wherein said first weld (S1) and said second weld (S2) are welds produced by addition of metal.

2. The bioreactor as claimed in claim 1, wherein first weld comprises a metal welding bead, or a plurality of welding beads and wherein second weld comprises a metal welding bead, or a plurality of welding beads and wherein,
    the or each metal welding bead of said first weld (S1) and/or of said second weld (S2) each forms a hollow fillet (11), said welds being polished.

3. The bioreactor as claimed in claim 1, wherein each of the bores (7) opens at an edge of the support (6) or of one of said supports (6).

4. The bioreactor as claimed in claim 3, wherein the bores (7) open towards the center of the container body (2).

5. The bioreactor as claimed in claim 3, wherein said first weld (S1) is constituted by a continuous welding line with a closed trajectory which runs at the edges of the bore (7) of the two sides (C1,C2) of said corresponding support (6), as well as on the cant (60) of said corresponding support (6), at the upper part and at the lower part of said cooling and/or heating duct; (3,3',3").

6. The bioreactor as claimed in claim 3, wherein the connectors (5) have a semi-tubular form, and wherein said second weld (S2) is constituted by a continuous welding line with a closed trajectory which runs at the edges of the connector, along the longitudinal edges (52) of the connector (5), as well as along the arched edges (51) of said connector.

7. The bioreactor as claimed in claim 1, with agitation means comprising: a rotor (8) inside the container body (2), which rotor is mobile in rotation relative to the container body (2), the rotor having blades (80); counter-blades (81) which project towards the center of the container, and are rendered integral in fixed positions relative to the container body (2).

8. The bioreactor as claimed in claim 7, wherein the counter-blades (81) of said agitation means comprise said support (6) or said supports (6) of said securing means.

9. The bioreactor as claimed in claim 1, wherein the bores (7) are so-called first bores, said support(s) (6) having, in addition to said first bores (7) at said various positions for receipt of the helicoid, second bores (9) with dimensions which are larger than the diameter of said duct, said duct passing through said second bores (9) such as to leave play which permits free deformation of said duct.

10. The bioreactor as claimed in claim 1, with a plurality of said supports (6) distributed angularly on the inner circumference of the container body, and each oriented along their longitudinal axis according to the height of the container body, and each extending corresponding to the height of the helicoid.

11. The bioreactor as claimed in claim 1, wherein said support (6) or each of the supports (6) has an outer edge facing the lateral inner wall (20) of the container (2), and wherein said securing means (4) comprise counter-braces (10) which ensure that said support (6) or each of said supports is rendered integral with the inner wall of the container body, creating an inter-space (It) between the outer edge (61) of said corresponding support (6) and the inner wall (20) of the container body.

12. The bioreactor as claimed in claim 11, wherein each counter-brace (10) is welded respectively on the corresponding support (6) and on the inner wall (20) of the container body (2), and wherein, by means of addition of metal, said welds have a metal welding bead forming a hollow fillet, said welds being polished.

13. The bioreactor as claimed in claim 1, provided with a device for cooling/heating the container body from the exterior, by means of circulation of a fluid which conveys heat/cold.

14. The bioreactor as claimed in claim 1, wherein the or each of the supports (6) is selected from amongst a plate (62) or a profile (63).

15. A method for biological or biochemical reactions, comprising adding a biological catalyst and nutritive substances to the bioreactor according to claim 1.

16. The method according to claim 15, wherein said biological or biochemical reactions produce microalgae *Chlorella*.

17. The use method according to claim 15, wherein said biological or biochemical reactions are in the field of the human or animal foodstuffs industries, biotechnology industries, pharmaceutical and cosmetics industries, and in the field of biofuels and chemistry.

\* \* \* \* \*